United States Patent [19]

Larock

[11] 4,105,705

[45] Aug. 8, 1978

[54] SYMMETRICAL BIARYL SYNTHESIS VIA RHODIUM CATALYZED DIMERIZATION OF ARYL MERCURIC SALTS

[75] Inventor: Richard Craig Larock, Ames, Iowa

[73] Assignee: Iowa State University Research Foundation, Inc., Ames, Iowa

[21] Appl. No.: 754,116

[22] Filed: Dec. 27, 1976

Related U.S. Application Data

[63] Continuation-in-part of Ser. No. 681,783, Apr. 30, 1976, Pat. No. 4,026,957.

[51] Int. Cl.$^2$ .............................................. C07C 15/00
[52] U.S. Cl. ............................ 260/668 R; 260/666 B; 260/515 R; 260/453 R; 260/563 R; 260/586 R; 260/680 B; 568/730
[58] Field of Search .................................... 260/668 R

[56] References Cited

U.S. PATENT DOCUMENTS

| | | | |
|---|---|---|---|
| 3,361,840 | 1/1968 | Kohll et al. | 260/680 B |
| 4,026,957 | 5/1977 | Larock | 260/668 R |

*Primary Examiner*—Veronica O'Keefe
*Attorney, Agent, or Firm*—Zarley, McKee, Thomte, Voorhees & Sease

[57] ABSTRACT

Vinyl- and arylmercuric halide salts undergo reaction with rhodium (I) and (III) catalysts, preferably in the presence of lithium chloride to provide essentially quantitative yields of the corresponding 1,3 dienes and biaryls respectively. Importantly, the reaction is stereospecific and is especially valuable for synthesis of symmetrical functionally substituted dienes, biaryls and polyenes.

16 Claims, No Drawings

SYMMETRICAL BIARYL SYNTHESIS VIA RHODIUM CATALYZED DIMERIZATION OF ARYL MERCURIC SALTS

CROSS REFERENCE TO A RELATED APPLICATION

This application is a continuation in part of earlier filed copending application Ser. No. 681,783, filed Apr. 30, 1976 now U.S. Pat. No. 4,026,957 issued May 31, 1977.

BACKGROUND OF THE INVENTION

Conjugated dienes are of considerable importance in organic chemistry in and of themselves. In addition, they are extremely important for use in the well known Diels-Alder reaction. Many conjugated dienes, biaryls and polyenes are used as intermediates for synthesis reactions and as monomers for the formation of polymeric reaction products. For example, the preparation of polybutadiene rubber.

One problem often encountered with prior art processes for the formation of conjugated dienes is that the reaction procedures often are unsuitable for the preparation of functionally substituted dienes. Thus, if the diene being prepared is functionally substituted with, for example, a carboxyl group, a carbonyl group, an amino group, an ester group, or the like, often the reactive site in any synthesis reaction will be at the functional group rather than the formation of the desired conjugated diene. As a result, very few functional groups have been incorporated into these reactions.

In addition, the preparation of conjugated dienes often encounters the difficulty that the stereospecificity of the reaction starting material is lost in the coupling procedure to prepare the conjugated diene. This is important in many syntheses since the stereochemistry can and indeed often does affect the ultimate reaction properties of any polymers which are formed.

Accordingly, there is a real need in the art for the development of a new process for the preparation of symmetrical conjugated dienes and polyenes which both tolerates functionality and which produces symmetrical dienes, stereospecifically, in high yields. This invention has as one of its primary objectives the satisfaction of the above described needs, with respect to synthesis of conjugated dienes by a catalytic synthesis procedure.

My earlier application related to a useful new method for the symmetrical dimerization of readily available vinylmercuric chlorides which employed stoichiometric amounts of palladium chloride and lithium chloride and provided 1,3-dienes in excellent yield. It has now been found that similar results can be achieved by use of rhodium catalysts thereby eliminating the previously required stoichiometric amount of expensive palladium chloride.

It has also been discovered that nearly quantitative yields of biaryl compounds can be obtained by dimerization of aryl-mercurials in accord with a similar rhodium catalyzed reaction.

SUMMARY OF THE INVENTION

In summary, the invention provides for the first time a convenient, stereospecific, rhodium catalyzed synthesis of 1,3 dienes, and biaryls via vinylmercurials and arylmercurials, respectively.

Importantly, reactions occur without any adverse effect upon functionally substituted groups.

DETAILED DESCRIPTION OF THE INVENTION

In accordance with the process of this invention for synthesis of dienes from vinylmercurials, a vinylmercuric halide of the general formula

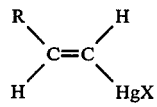

is dimerized in the presence of a rhodium (I) or (III) catalyst. In the formula for the vinylmercuric halide, X represents the anion of that compound and may be any of the common inorganic anions such as nitrate, acetate, phosphate, sulfate, chloride, bromide, iodide or the like. However, it is most preferable that X represents a monovalent inorganic anion which is a halide and more particularly is either chloride, bromide or iodide.

The value of R is not critical and depends upon the precise conjugated diene which one desires to prepare. Generally R may be hydrogen or an organic hydrocarbon radical which is either saturated or unsaturated. The radical may be functionally substituted to provide, for example, keto groups, carboxylic acid groups, hydroxy groups, ester groups, amino groups, or other functional substituents. It may be an alkyl, acyl, aryl, aralkyl, alkenyl, alkynyl, straight or branched chains, or cyclic derivatives of the above, including heterocyclics.

Preferably R is a lower, $C_{12}$ and below, saturated or unsaturated, substituted or unsubstituted, alkyl, alkenyl, phenyl, or aralkyl group.

As depicted in the general formula for the vinylmercuric halide salt, two hydrogen moieties are shown. However, it is to be understood that, if desired, the hydrogen moieties may be replaced with organic radicals such as those previously described to represent R.

The starting material for the diene synthesis reaction of this invention, namely, vinylmercuric halides, are readily available through acetylene addition reactions, see for example, R. C. Larock and H. C. Brown, *J. Organometal Chem.*, 36, 1 (1972).

R. C. Larock, S. K. Gupta, and H. C. Brown, *J. Amer. Chem. Soc.*, 94, 4371 (1972).

H. Staub, K. P. Zeller and H. Leditschke, In Houben-Weyl's "Methoden der Organischen Chemie", Fourth Ed., Vol. 13, G. Thieme Verlag, Stuttgart, 1974, Pt. 2b, pp. 192–199.

which are incorporated herein by reference.

Turning now to the biaryl synthesis, the starting materials are arylmercurials, ArHgX or Ar$_2$Hg, preferably arylmercurial halide salts. Biaryls are usually prepared by the dimerization of aryl halides by copper (Ullmann reaction) or zerovalent nickel reagents, or through the reaction of aromatic Grignard or lithium reagents, with any variety of inorganic salts. The Ullmann reaction suffers several disadvantages. It is best carried out with aryl iodides which are often difficult to obtain in high isomeric purity. It is incompatible with amine, amide, and hydroxyl functionality, and it usually requires basic solvents and temperatures in excess of 200° C for extended reaction times. The nickel (O) reagents are not readily available and are difficult to handle. The use of the highly reactive arylmagnesium and -lithium reagents is limited by the incompatibility of these organometallics with a variety of important organic functional groups.

It has now been found, just like the dimerization of vinylmercurials with rhodium catalyzed reactions, the corresponding reaction of arylmercuric salts in the presence of rhodium catalysts can be used to achieve a new route to biaryls.

The aryl compound (ArHgX) has the same X moiety as the vinylmercuric compound. The aryl moiety may be alkylaryl, a functionally substituted aryl such as a keto, hydroxy, nitro, sulfur, or oxygen substituted aryl, it may be a naphthalene ring containing compound, an anthracene ring containing compound, a diaryl compound or the like. Preferably, it is an aryl, either functionally substituted or non-substituted, or a $C_1$-$C_{12}$ alkylaryl mercurial compound.

The catalyst for the dimerization reactions described herein is either a rhodium (I) or (III) catalyst and is preferably a rhodium I or rhodium III complex. Using such catalysts vinylmercuric salts and arylmercuric salts are dimerized in high yield and isomeric purity.

The catalyst may be rhodium per se but is preferably a rhodium salt and is most preferably a rhodium (I) or (III) complex. Rhodium I complex salts are well known and are generally prepared by the reduction of rhodium (III) salts in the presence of a selected ligand such as phosphines, dienes, carbon monoxide and the like. Such complexes are readily available from specialty chemical houses and by synthesis in accordance with the Osborne et al. article, which is incorporated by reference in a later part of this application.

The amount of catalyst may vary from 0.01% up to about 10% of an equivalent of the vinylmercuric salt or the arylmercuric salt depending upon whether the reaction is conducted in the presence of certain organic solvents or in the presence of an added source of chloride ions, such as lithium chloride. Where added chloride ion source is employed, i.e., over and above the amount from the vinyl or aryl salt, catalyst amounts on the lower end of the range may be employed.

Any polar organic solvent capable of dissolving the catalyst and the aryl or vinylmercuric salt may be employed, but it has been found that the yield increases steadily with the polarity of the solvent, and in particular, seems to be best when the solvent is an organic phosphorous containing solvent. Typical solvents which may be employed to produce the biaryl and diene products of this invention include tetrahydrofuran, acetonitrile, pyridine, acetone, methyl alcohol, dimethyl sulfoxide, N, N-dimethyl formamide, and organic phosphorous containing polar solvents such as hexamethylphosphoramide. The preferred solvent is hexamethylphosphoramide since the highest yields of product, consistent with maintaining stereospecificity, are achieved.

As previously mentioned, in order to achieve high yields of the symmetrical conjugated dienes, or biaryls in accord with the synthesis reaction, it is preferred that reaction be conducted in the presence of added amounts of halide ions. By the term added amounts of halide ions is meant amounts of halide ions in excess of the amount which may otherwise be provided by the aryl or vinylmercuric salt, if that salt is a halide salt. It is preferred that additional amounts of halide ions be added because such has been found essential to providing high yields of symmetrical conjugated dienes and biaryls which maintain the stereochemistry of the aryl or vinylmercuric salt. The source of the additional halide ions may be any metal salt which is soluble in the reaction solvent. Preferably the metal salt is an alkali metal halide salt with the alkali metal being sodium, potassium or lithium. Most preferably the alkali metal is lithium and the salt is lithium chloride.

It is preferred that the reaction be conducted at room temperature or lower temperatures for preparation of conjugated dienes. Generally satisfactory results are obtained at temperatures within the range of from about 0° C to about 25° C with satisfactory results being obtained at room temperature. However, for dimerization of arylmercurials it is preferred that the reaction be within the range of 60° C to 90° C and preferably 70° C to 85° C.

To summarize for a moment, the synthesis route for the preparation of the symmetrical, stereospecific, conjugated dienes in accord with the process of this invention may be represented by the following equation, which assumes that the vinylmercury compound is a vinylmercuric chloride, and which assumes that the rhodium catalyst employs added amounts of lithium chloride as an additional chloride ion source.

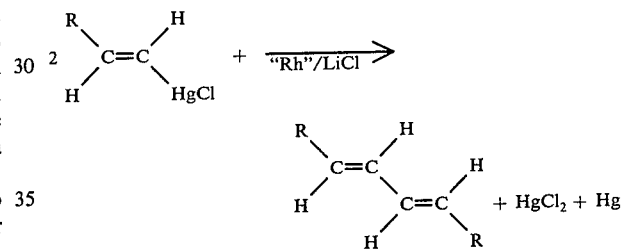

The reaction is advantageous over prior art processes of preparing conjugated dienes in that it obtains the desired product in high yield, often in excess of 90%. In addition, the reaction is stereospecific and maintains the stereospecific relationship of the vinylmercuric halide so that one can predictably prepare cis or trans isomers. In addition, the reaction is highly tolerant of the presence of functional groups substituted on the R moiety or in place of the hydrogen moieties of the vinylmercuric salt. It is the entire combination of reaction conditions which produces high yields, the tolerance to functional groups, and the stereospecificity. The obtaining of high yields and control of the stereochemistry of the isomer produced appears to be a function of the organomercuric halide starting material in combination with suitable solvents. It is preferred that the reaction temperature be room temperature or lower since better yields and higher stereospecificity are observed at lower temperatures.

The overall reaction for dimerization of the biaryls may be represented as follows:

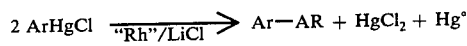

This reaction has all of the advantages previously listed for the vinylmercurial dimerization reaction.

The following examples are offered to further illustrate but not limit the process of this invention.

EXAMPLES OF SYNTHESIS OF DIENES VIA VINYLMERCURIALS AND RHODIUM CATALYSIS

In these initial examples the effect of 10% of a variety of commercially available rhodium(I) and (III) complexes on the room temperature dimerization of trans-1-hexenylmercuric chloride in HMPA (equation below) was studied. The results are summarized in Table 1.

Table 1.

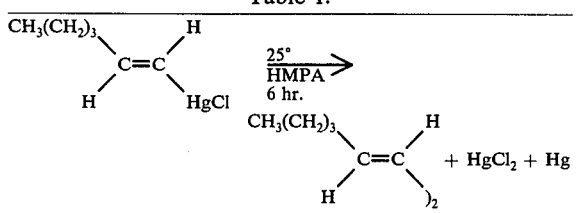

RHODIUM CATALYZED DIMERIZATION OF TRANS-1-HEXENYLMERCURIC CHLORIDE[a]

| Examples | Rhodium Complex | Diene Yield (%)[b] |
|---|---|---|
| 1 | ClRh(PPh$_3$)$_3$ | 28 |
| 2 | ClRh(CO)(PPh$_3$)$_2$ | 74 |
| 3 | [ClRh(CH$_2$=CH$_2$)$_2$]$_2$ | 70 |
| 4 | [ClRh(COD)]$_2$[c] | 81 |
| 5 | [ClRh(CO)$_2$]$_2$ | 87 |
| 6 | [ClRh(CO)$_2$]$_2$/LiCl[d] | 95 |
| 7 | RhCl$_3$ . nH$_2$O[e] | 61 |
| 8 | RhCl$_3$ . nH$_2$O[e]/LiCl[d] | 94 |

[a] All reactions were run with 10% "rhodium" per vinylmercurial (5% dimeric rhodium complex) for 6 hours at room temperature in HMPA (hexamethylphosphoramide) under a nitrogen atmosphere.
[b] All yields were determined by GLC analysis using an internal standard.
[c] COD = 1,5-cyclooctadiene.
[d] Two equivalents of lithium chloride per vinylmercurial were employed.
[e] n is approximately 2.3.

All of the rhodium complexes studied proved to be catalytic. The rhodium (I) complexes generally appear to be more effective than rhodium trichloride. In all reactions, the trans,trans-diene was obtained in 98% or greater stereospecificity. Unlike the earlier palladium reactions of my parent application, low temperatures are no longer necessary to achieve high stereospecificity. While the large majority of the diene product is formed in the first 6 hours, the yields can be slightly improved by letting the reaction run longer (up to 24 hours). As in my earlier application work with palladium chloride, the addition of lithium chloride (2 equiv. per vinylmercurial) can substantially improve the yield of diene. The combination of lithium chloride and [ClRh(CO)$_2$]$_2$ or RhCl$_3$.nH$_2$O appeared to be the most effective catalyst. A comparison of these two complexes at various catalyst concentrations demonstrated the superiority of the rhodium (I) complex (Table II). Even at concentrations as low as 0.01% and in the presence of air, this catalyst gives a 95% yield of trans,trans-5,7 dodecadiene from trans-1-hexenylmercuric chloride. The effect of other solvents on this reaction was not significant, it was found that one need not use HMPA since diethyl ether or tetrahydrofuran (THF) work equally well. (Table II).

The full scope of this reaction has been investigated on a variety of vinylmercuric chlorides, and the yields are indicated in Table III. Vinylmercurials derived from terminal alkynes give excellent yields of the corresponding dienes. The more sterically hindered vinylmercurials derived from internal alkynes react much more sluggishly and even after heating at 75° C for 24 hours still give only very poor yields of 1,3-dienes.

Table II.

Comparison of Rhodium Catalyst Activity $$2 \; \underset{H}{\overset{CH_3(CH_2)_3}{>}}C=C\underset{HgCl}{\overset{H}{<}} \longrightarrow \underset{H}{\overset{CH_3(CH_2)_3}{>}}C=C\underset{)_2}{\overset{H}{<}}$$

| Ex. | Rhodium Catalyst | Solvent | Concentration(%)[a] | Yield (%)[b] |
|---|---|---|---|---|
| 9 | RhCl$_3$ . nH$_2$O[c]/LiCl | HMPA | 10 | 100 |
| 10 | | | 1 | 85 |
| 11 | [ClRh(CO)$_2$]$_2$/LiCl | | 10 | 98 |
| 12 | | | 1 | 100 |
| 13 | | | 0.01 | 90 |
| 14 | | | | 95[d] |
| 15 | | Et$_2$O | 1 | 90 |
| 16 | | THF | | 78[e] |
| 17 | | | | 99 |

[a] Percent "rhodium" per vinylmercurial.
[b] Analysis by GLC using an internal standard.
[c] n is approximately 2.3.
[d] Reaction run in the presence of air (all others are under nitrogen).
[e] No lithium chloride used.

Table III.

Synthesis of Dienes and Polyenes

| Example | Vinylmercurial | Catalyst[a] | Solvent | Diene | Yield (%)[b] |
|---|---|---|---|---|---|
| 18 | C$_6$H$_5$-CH=CH-HgCl | RhCl$_3$ . nH$_2$O | HMPA | (C$_6$H$_5$-CH=CH-)$_2$ | 65 |
| 19 | | [ClRh(CO$_2$)]$_2$ | | | 100 |
| 20 | | | THF | | 84 |
| 21 | CH$_3$(CH$_2$)$_3$-CH=CH-HgCl | RhCl$_3$ . nH$_2$O | HMPA | (CH$_3$(CH$_2$)$_3$-CH=CH-)$_2$ | 85 |
| 22 | | [ClRh(CO)$_2$]$_2$ | | | 100 |
| 23 | | | THF | | 99 |
| 24 | (CH$_3$)$_3$C-CH=CH-HgCl | RhCl$_3$ . nH$_2$O | HMPA | ((CH$_3$)$_3$C-CH=CH-)$_2$ | 98 |
| 25 | | [ClRh(CO)$_2$]$_2$ | | | 100(88) |
| 26 | | | THF | | 100 |

Table III.-continued

| | | Synthesis of Dienes and Polyenes | | | |
|---|---|---|---|---|---|
| Example | Vinylmercurial | Catalyst[a] | Solvent | Diene | Yield (%)[b] |
| 27 | CH₃CH₂\C=C/CH₂CH₃  H/    \HgCl | RhCl₃·nH₂O | HMPA | (CH₃CH₂\C=C/CH₂CH₃  H/    \)₂ | 24[c] |
| 28 | | [ClRh(CO)₂]₂ | | | 35[c] |
| 29 | Cy\C=C/H  H/  \HgCl | | | (Cy\C=C/H  H/  \)₂ | (90) |
| 30 | | | THF | | (97) |
| 31 | cyclohexenyl\C=C/H  H/  \HgCl | | HMPA | (cyclohexenyl\C=C/H  H/  \)₂ | (92) |

[a]1% "Rhodium" and 2 equiv lithium chloride per vinylmercurial;
[b]GLC analysis (isolated yield);
[c]Reactions run at 75° C.

EXAMPLES OF BIARYL SYNTHESIS

Using conditions similar to those worked out for the synthesis of dienes ([ClRh(CO)₂]₂ and lithium chloride), the effect of different catalyst concentrations, temperatures, and solvents on the dimerization of both phenylmercuric chloride and diphenylmercury (Table IV) was studied. Phenylmercuric chloride proved significantly less reactive than any of the vinylmercuric chlorides examined earlier and reaction temperatures greater than room temperature were required to obtain a reasonable rate of reaction. A reaction temperature of 80° C was quite sufficient and all subsequent work was done at this temperature. Catalyst concentrations as low as 1% proved effective. Increasing or decreasing the amount of catalyst resulted in lower yields of biphenyl. Polar solvents proved most effective, with acetonitrile somewhat less effective than HMPA.

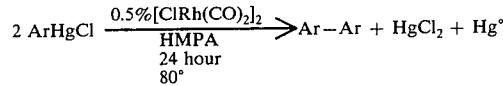

$$2\ ArHgCl\ \xrightarrow[\substack{HMPA\\24\ hour\\80°}]{0.5\%[ClRh(CO)_2]_2}\ Ar-Ar + HgCl_2 + Hg°$$

(Table V) was studied. In general, the yields of biaryl are comparable to those obtained by other routes. However, the reaction proceeds at much lower temperatures than the Ullmann reaction and significantly lower than those of Kretchmer's procedure.

Table V.

| | Synthesis of Biaryls | | | |
|---|---|---|---|---|
| Example | Arylmercuric Chloride | Biaryl | Isolated Yield (%) | Mp(° C) (lit mp) |
| 43 | Ph—HgCl | (Ph—)₂ | 84 | 62–65.5 (70.5) |

Table IV.

| | [ClRh(CO)₂]₂ Catalyzed Dimerization of Arylmercurials[a] | | | | | |
|---|---|---|---|---|---|---|
| Example | Arylmercuric chloride[b] | Biaryl | Solvent | Catalyst concentration(%)[c] | Temp (° C) | Yield (%)[d] |
| 32 | Ph—HgCl | (Ph—)₂ | THF | 1 | 66 | 15[e] |
| 33 | | | | | | 25 |
| 34 | | | MeOH | | 65 | 24 |
| 35 | | | CH₃CN | | 82 | 65 |
| 36 | | | HMPA | 1 | 25 | 25 |
| 37 | | | | 0.5 | 80 | 61 |
| 38 | | | | 1 | | 81 |
| 39 | | | | 2 | | 67 |
| 40 | | | | 1 | 125 | 78 |
| 41 | | | | 1 | 25 | 36 |
| 42 | (Ph—)₂Hg | | | 1 | 80 | 66 |

[a]All reactions were run for 24 hr. with 2 equiv lithium chloride per arylmercurial under a nitrogen atmosphere.
[b]One mmol phenylmercuric chloride or 0.5 mmol diphenylmercury.
[c]Percent "rhodium" per vinylmercurial.
[d]GLC analysis using an internal standard.
[e]No lithium chloride present.

The generality of the above described approach to the synthesis of biaryls (equation below)

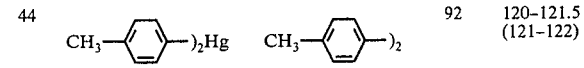

| 44 | CH₃—Ph—)₂Hg | CH₃—Ph—)₂ | | | | 92 | 120–121.5 (121–122) |

Table V.-continued
Synthesis of Biaryls

| Example | Arylmercuric Chloride | Biaryl | Isolated Yield (%) | Mp(° C) (lit mp) |
|---|---|---|---|---|
| 45 | CH$_3$O—〈 〉—HgCl | CH$_3$O—〈 〉—)$_2$ | 88 | 177–178 (175) |
| 46 | HO—〈 〉—HgCl | HO—〈 〉—)$_2$ | 88 | 277–278.5 (272) |
| 47 | NO$_2$-〈 〉—HgCl | NO$_2$-〈 〉—)$_2$ | 53 | 202–202.5 (200) |
| 48 | 〈 〉—〈 〉—HgCl | 〈 〉—〈 〉—)$_2$ | 40 | 312–313 (320) |
| 49 | (naphthyl)—HgCl | (naphthyl)—)$_2$ | 94 | 185–186 (187–8) |
| 50 | (furyl-O)—HgCl | (furyl-O)—)$_2$ | 70 | oil |
| 51 | (thienyl-S)—HgCl | (thienyl-S)—)$_2$ | 96 | 32–33 (32.5) |

The ease with which arylmercurials are obtained through direct electrophilic aromatic mercuration of arenes and the high isomeric purity obtained by simple recrystallization of these stable organometallics recommends their use in organic synthesis. The mild conditions for dimerization and ease of isolation, plus the high isomeric purity of the products makes this a valuable new route to symmetrical biaryls.

The following general procedures are repeated herein only once to show the exact procedure employed for the preparation of the rhodium catalyzed dienes and binaryls shown in the above tables.

Reagents

All chemicals were used directly as obtained commercially unless otherwise indicated. HMPA was distilled from lithium aluminum hydride (LAH) under vacuum. Pentane was stirred over fuming sulfuric acid, washed with water and stored over anhydrous sodium sulfate after distillation. Ether and THF were distilled from LAH.

The vinylmercurials used have all been described elsewhere in this application and my earlier parent case, and were prepared using a standard hydroboration-mercuration sequence as shown discussed in the incorporated references.

[ClRh(CO)$_2$]$_2$ (PCR), [(CH$_2$=CH$_2$)$_2$RhCl]$_2$ (Strem), (1,5-COD RhCl)$_2$ (ROC/RIC), (Ph$_3$P)$_2$Rh(CO)Cl (Alfa Inorganics-Ventron), and RhCl$_3$.nH$_2$O (Matthey Bishop) were used directly as obtained. Wilkinson's catalyst, (Ph$_3$P)$_3$RhCl, was prepared from RhCl$_3$.nH$_2$O according to published procedures of Obsborne, et al., Inorganic Synthesis, 10, 67 (1967) which is incorporated herein by reference.

All GLC yields are corrected by the use of appropriate hydrocarbon internal standards.

(Rhodium Catalyzed Dimerization of trans-1-Hexenylmercuric Chloride — Table I)

The catalytic activity of a variety of different rhodium catalysts was examined using the following standard procedure for the dimerization of trans-1-hexenylmercuric chloride. The catalyst (0.10 mmol of monomeric, and 0.05 mmol of dimeric rhodium catalysts), tetradecane ((internal standard, approx. 0.5 mmol) and lithium chloride (2.0 mmol) where appropriate were dissolved in HMPA 5 ml) in a 25 ml round bottom flask which has been previously flushed with nitrogen. The trans-1-hexenylmercuric chloride (1.00 mmol) was added and the reaction stirred for 6 hours at room temperature. Ether (5 ml) was then added and the mixture analyzed on a 10′ 10% DC-550 GLC column. The results are included in Table I.

(Comparison of Rhodium Catalyst Activity—Table II)

The appropriate amount of RhCl$_3$.nH$_2$O ($n \simeq 2.3$) (0.1 or .01 mmol) or [ClRh(CO)$_2$]$_2$ (0.05, 0.005 or 0.00005 mmol), lithium chloride (2 mmol), and tetradecane were dissolved in 5 ml of the appropriate solvent. Trans-1-hexenylmercuric chloride (1 mmol) was added and the reaction stirred for 24 hours at room temperature. The yields in HMPA were determined by GLC as described above. The ether and THF reactions were analyzed by GLC after adding water or saturated ammonium chloride solution respectively. 0.01% [ClRh(CO)$_2$]$_2$ was achieved by adding 0.025 ml. of a solution containing 4.0 mg. of catalyst in 5.0 ml. HMPA. The results are summarized in Table II.

(Synthesis of Dienes)

The following procedure for the synthesis of trans,-trans-2,2,7,7-tetramethylocta-3,5-diene, is representative. [ClRh(CO)$_2$]$_2$ (0.05 mmol) and lithium chloride (20 mmol) were placed in a 250 ml round bottom flask equipped with a septum inlet and gas inlet tube which has been flushed with nitrogen. HMPA (50 ml) and then trans-3,3-dimethyl-1-butenyl-mercuric chloride (10.0 mmol) were added and the reaction stirred for 24 hours at room temperature. The reaction mixture was poured into water and pentane added. A gray suspension formed and was filtered off. The gray residue was washed with pentane. The pentane layer was separated and the water layer re-extracted with pentane. The combined pentane extracts were washed with water, dried over anhydrous sodium sulfate, and the pentane removed under vacuum. A white solid (0.73 g, 88%, crude mp 74°–77° C, mp 77°–78° C (EtOH), lit. mp. 78°–79° C) was obtained. $^1$H NMR (CCl$_4$) $\delta$1.00 (18H, s, CH$_3$) and 5.6 (4H, m, vinyl). All other dienes were prepared in like manner using the same molar quantities, solvent and conditions. The results are reported in Table III.

The THF preparative reaction was worked up by adding saturated ammonium chloride, separating the layers, and washing the aqueous layer with hexane. The combined organic layers were then washed with saturated ammonium chloride, 3M sodium thiosulfate, and saturated sodium chloride, dried over anhydrous sodium sulfate, and the solvent removed.

All GLC yields were determined on reactions run on one-tenth the above scale following GLC analysis procedures identical to those outlined above. Internal standard correction factors were determined using authentic diene samples.

([ClRh(CO)$_2$]$_2$ Catalyzed Dimerization of Arylmercurials—

The effect of catalytic amounts of [ClRh(CO)$_2$]$_2$ on the dimerization of phenylmercuric chloride and diphenylmercury was examined as follows: The appropriate quantity of [ClRh(CO)$_2$]$_2$ (0.01, 0.005 and 0.0025 mmol), lithium chloride (2.0 mmol) and octadecane were dissolved in the appropriate solvent (5 ml) in a 25 ml round bottom flask equipped with a rubber septum. After adding phenylmercuric chloride (1.0 mmol) or diphenylmercury (0.50 mmol) the reaction was stirred for 24 hours at room temperature or in a preheated oil bath. The HMPA reaction was poured into water and ether added. The ether layer was analyzed by GLC on a 10′ 10% DC-550 column. The THF reactions were analyzed as described previously and the methanol and acetonitrile reactions were analyzed directly.

(Synthesis of Biaryls — Table V)

The following procedure for the synthesis of 4,4′-bianisole is representative. [ClRh(CO)$_2$]$_2$ (0.05 mmol) and lithium chloride (20 mmol) were dissolved in HMPA (50 ml) in a 250 ml round bottom flask equipped with a gas inlet tube and a sidearm fitted with a rubber septum. After adding 4-methoxyphenylmercuric chloride (10 mmol) the reaction was stirred in a preheated oil bath at 80° C for 24 hours. A puddle of metallic mercury was observed. The reaction mixture was then poured onto ice and benzene added. After separating the layers, the water was re-extracted with benzene. The combined organic layers were washed with water, 10% HCl, 3M sodium thiosulfate, water and saturated sodium chloride, and dried over anhydrous magnesium sulfate. Removal of the solvent under vacuum provided 0.94 g of white solid (88%); mp 174.5°–175.5° C before recrystallization, mp 177°–178° C (hexane) (lit. mp. 175° C).

As has been mentioned previously herein and as shown in Examples 41, 42 and 44, while the preferred arylmercuric salts are the arylmercuric halide salts, satisfactory results are also obtained when diarylmercury salts (Ar)$_2$Hg are employed, as for example diphenylmercury and di-p-tolylmercury. Thus, it is to be understood that the specific description given herein for arylmercuric salts is also equally applicable to the diarylmercury salts.

What is claimed is:

1. A method of preparing symmetrical biaryl compounds, said method comprising, dimerizing an aryl mercuric compound selected from the group consisting of aryl mercuric halide salts and diaryl mercuric compounds by contacting said aryl mercuric compound with a catalytically effective dimerization inducing amount of a rhodium catalyst.

2. The method of claim 1 wherein said arylmercuric compound is an alkylaryl compound.

3. The method of claim 2 wherein said rhodium catalyst is rhodium metal.

4. The method of claim 3 wherein said catalyst is a rhodium salt.

5. The method of claim 4 wherein said catalyst is a rhodium halide salt.

6. The method of claim 5 wherein said rhodium catalyst is a rhodium organic compound complex salt.

7. The method of claim 6 wherein said rhodium complex is a rhodium (I) organic complex salt with the anion of said salt being a halide.

8. The method of claim 7 wherein said reaction is conducted in the presence of an additional source of halide ions.

9. The method of claim 8 wherein said source of additional halide ions is an alkali metal halide salt.

10. The method of claim 9 wherein said salt is lithium chloride.

11. The method of claim 1, wherein the amount of said rhodium catalyst is an amount within the range of from about .01% of an equivalent of said arylmercuric compound up to about 10% of an equivalent of said arylmercuric compound.

12. The method of claim 11 wherein said reaction is conducted in the presence of a polar organic solvent.

13. The method of claim 12 wherein said reaction is conducted in the presence of a phosphorous containing polar organic solvent.

14. The method of claim 1 wherein said dimerizing reaction is conducted at a temperature within the range of from about 60° C to about 90° C.

15. The method of claim 1 wherein said reaction is conducted at a temperature within the range of from about 70° C to about 85° C.

16. A method of claim 1 wherein said aryl mercuric compound has a $C_{1-12}$ alkyl side chain attached to the aromatic ring structure of said aryl compound.

* * * * *